(12) United States Patent
Sato et al.

(10) Patent No.: US 6,740,782 B2
(45) Date of Patent: May 25, 2004

(54) SULFUR COMPOUNDS AND INTERMOLECULAR COMPOUNDS CONTAINING THE SAME AS THE COMPONENT COMPOUNDS

(75) Inventors: Ryu Sato, Morioka (JP); Hiroshi Suzuki, Chiba (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 10/221,757

(22) PCT Filed: Mar. 14, 2001

(86) PCT No.: PCT/JP01/02004

§ 371 (c)(1),
(2), (4) Date: Sep. 12, 2002

(87) PCT Pub. No.: WO01/68595

PCT Pub. Date: Sep. 20, 2001

(65) Prior Publication Data

US 2003/0130358 A1 Jul. 10, 2003

(30) Foreign Application Priority Data

Mar. 14, 2000 (JP) .......................................... 2000-069760
Sep. 14, 2000 (JP) .......................................... 2000-279966

(51) Int. Cl.$^7$ ...................... C07C 317/00; C07C 321/00
(52) U.S. Cl. ............................ 568/29; 568/28; 568/57; 568/67; 568/27
(58) Field of Search ............................ 568/27, 28, 38, 568/57, 61, 67

(56) References Cited

U.S. PATENT DOCUMENTS 5,364,977 A 11/1994 Asai et al.

FOREIGN PATENT DOCUMENTS

| JP | 62-184012 | 8/1987 |
| JP | 3-132 | 1/1991 |
| JP | 11-43448 | 2/1999 |

OTHER PUBLICATIONS

CA:108:113789 abs of JP62184012 Aug. 1987.*
CA:117:27128 abs of Collections of Czeckoslovak Chemical Communications by Patek et al 57(3) pp508–24 1992.*
BRN 3504382 Beilstein abstract of J. Chem Soc by Mustafa pp 353–354 1949.*
CA:110:153792 abs of Chemische Berichte by Duennebacke et al 122(3) pp533–5 1989.*
CA:93:167805 abs of Indian Journal of Chemistry Section B by Tadros et al.*
CA; 111:56922 abs of Journal of American Chemical Society by Neumann 111(15) pp 5845–51.*
CA:84:104662 abs of Journal of Organic Chemistry by Pines, S. H. 41(5) pp 884–5 1976.*
CA:132:50622 abs of Journal of Applied Polymer Science by Meng et al 74(13) pp 3069–3077 1999.*

Yuezhonmeng et al., Crosslinking of poly (arylene disulfide)s and poly (arylene sulfane)s derived from cyclic (arylene disulfide) oligomers, 1999, vol. 74, No. 13, pp. 3069–3077.
Marcel Patek et al., Safety–catch protecting groups in peptide synthesis, Collect. Czech. Chem. Commun., 1992, vol. 57, No. 3, pp. 508–524.
Seemon H. Pines, reinvestigation of the acetylation of thioanisole. Effect of the mole ratio of aluminum chloride, J. Org. Chem, 1976, vol. 41, No. 5, pp. 884–885.
Hans Joerg Schneider et al., Host–guest supramolecular chemistry. 34. The incremental approach to noncovalent interactions: culomb and van der Waals effects in organic ion pairs, J. Am. Chem. Soc., 1992, vol. 114, No. 20, pp. 7684–7703.

* cited by examiner

Primary Examiner—Jean F Vollano
(74) Attorney, Agent, or Firm—Dennis G. LaPointe; Mason Law, P.A.

(57) ABSTRACT

The invention aims at providing novel sulfur compounds, molecular compounds containing the same as the component compound, and so on. The above aim is achieved by using sulfur compounds of the general formula (I) wherein Rs are each independently hydrogen, optionally substituted $C_{1-6}$ alkyl, optionally substituted $C_{2-6}$ alkenyl, optionally substituted aryl, chloro, or bromo; m is an integer of 0, 1, or 2; and Z is a group represented by any of the general formulae (II) to (V) (wherein R and m are each as defined above; W is hydrogen or $C_{1-6}$ alkyl; and Y is a direct bond, $C_{1-3}$ alkylene, or phenylene).

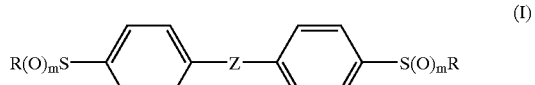

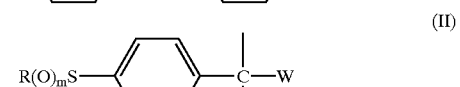

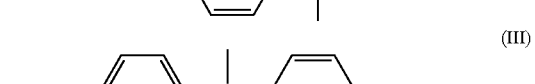

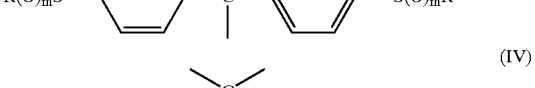

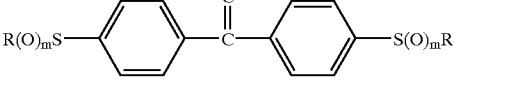

2 Claims, No Drawings

SULFUR COMPOUNDS AND INTERMOLECULAR COMPOUNDS CONTAINING THE SAME AS THE COMPONENT COMPOUNDS

The application is a 371 of PCT JP01/02004, filed Mar. 14, 2001, now WO 01/68595.

TECHNICAL FIELD

The present invention relates to a novel sulfur-containing compound and molecular compound comprising the sulfur-containing compound as a component compound.

BACKGROUND ART

Molecular compounds are compounds where two or more compounds are bonded via a comparatively weak interaction other than covalent bonds as typified by a hydrogen bond and by van der Waals force. Because molecular compounds have a quality that allows them to dissociate into original component compounds by a simple manipulation, recently, their application has been anticipated in such spheres as selective separation of useful substances, chemical stabilization, non-volatilization, sustained release formulation, pulverization and the like.

One example of specific molecular compounds includes a clathrate compound and, for example, Japanese Unexamined Patent Publication No. Hei-6-166646 discloses clathrate compounds of tetraxis phenols with various organic compounds.

However, no molecular compound has been found which has satisfactory performance in selective separation, chemical stabilization, non-volatilization, sustained release formulation, pulverization and the like, due to problems in that the compounds are readily disintegrated by changes in external factors such as heat and pH, and compounds are easily dissociated in solutions in the conventional art.

The subject of the present invention is to provide a novel molecular compound which exhibits excellent performance in technical spheres such as selective separation of useful substances, chemical stabilization, non-volatilization, sustained release formation, pulverization and the like.

DISCLOSURE OF THE INVENTION

As a result of intensive research to solve the above problems, it has been found that a novel sulfur-containing compound derivative having triphenyl or tetrakisphenylthio skeleton exhibits excellent performance in technical spheres such as selective separation of useful substances, chemical stabilization, non-volatilization, sustained release formulation, pulverization, and the like, thereby the present invention has been completed.

That is, the present invention relates to a sulfur-containing compound represented by formula (I):

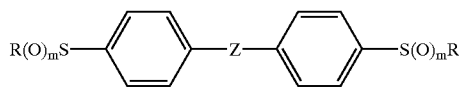

wherein each R independently represents a hydrogen atom, a C1 to C6 alkyl group which may have substituents, an alkenyl group which may have substituents, an aryl group which may have substituents, a chlorine atom or a bromine atom; m represents an integer of 0, 1, or 2; Z represents formulae (II) through (V):

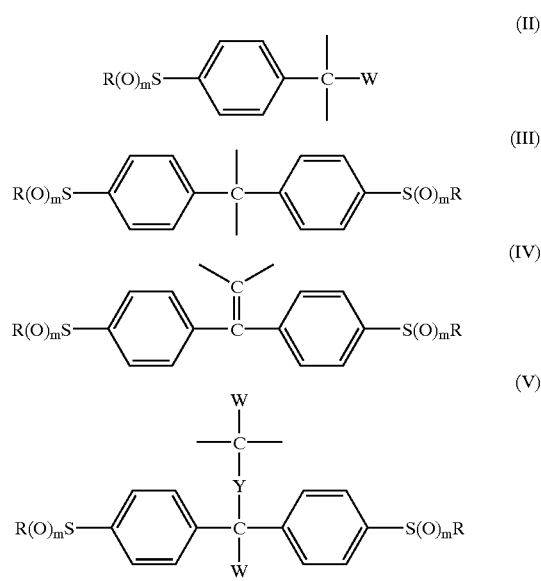

wherein R and m are the same as defined in the above; W represents a hydrogen atom, or a C1 to C6 alkyl group which may be substituted; and Y represents a direct bond, an alkylene group having 1 to 3 carbons, or a phenylene group.

The invention further relates to molecular compounds such as clathrate compounds comprising the sulfur-containing compound represented by the above formula (I) as a component compound, and to molecular compounds such as the above-mentioned clathrate compounds comprising as component compounds the sulfur-containing component as well as an anti-microbial agent, anti-fungal agent, insecticide, insect repellent agent, perfume, deodorant/anti-odor agent, anti-foulant, curing agent and curing accelerator for painting, resins and adhesives, natural essential oil, anti-oxidant agent, vulcanization accelerator or organic solvent which reacts with the sulfur-containing compound to form a molecular compound.

The molecular compound of the present invention is a compound where two or more component compounds which can each exist in a stable and independent manner are bonded through a comparatively weak interaction by other than covalent bonds as typified by a hydrogen bond and Van der Waals force, and includes hydrates, solvates, addition compounds, clathrate compounds and the like.

In the sulfur-containing compound represented by formula (I), the substituents represented by R can specifically include, for example, a hydrogen atom, straight-chain, branched or cyclic C1 to C6 alkyl groups such as methyl, n-propyl, isopropyl, n-butyl, isobutyl, t-butyl, n-hexyl, cyclohexyl groups and the like, alkenyl groups such as allyl, vinyl, 2-butenyl, 1-methylallyl groups and the like, aryl groups such as phenyl, 2-pyrizyl, 1,3-dimethyl-5-pyrazole groups and the like, a chlorine atom, a bromine atom, and the like.

The above C1 to C6 alkyl, C2 to C6 alkenyl, and aryl groups may be further substituted with a cyano group; a halogen atom such as a fluorine, chlorine and bromine atoms; and an aryl group such as a phenyl group.

In the formulae (II) through (V) which represent Z in the formulae (I), (VI) and (VII), the same substituents as the above can be exemplified as R, and W can specifically include, for example, a hydrogen atom, straight-chain, branched or cyclic C1 to C6 alkyl groups such as methyl, n-propyl, isopropyl, n-butyl, isobutyl, t-butyl, n-hexyl, cyclohexyl groups and the like, which may be further substituted with a fluorine atom, halogen atom and the like.

Y can include a direct bond, alkylene groups having 1 to 3 carbons such as methylene, ethylene, propylene and the like, or a phenylene group. Substituted positions in the phenylene group are not particularly limited, and either the 1,2 position, the 1,3 position or the 1,4 position may be substituted. Also, the phenylene group can have substituents thereon other than the necessary binding positions.

In the formulae (VI) and (VIII) of the present invention, R' can exemplify the same substituents as the aforementioned R.

And among the sulfur-containing compounds represented by formula (I) of the present invention, the compounds represented by formula (VI), particularly by the general formula (VIII) are preferable in terms of performances such as selective separation of useful substances, chemical stabilization, non-volatilization, sustained release formulation and pulverization. The compound represented by formula (VII) not only has clathrate ability but also is useful as an intermediate of the compound represented by formula (VI).

The compound of the present invention can be yielded by the following process for the production.
(Reaction 1)

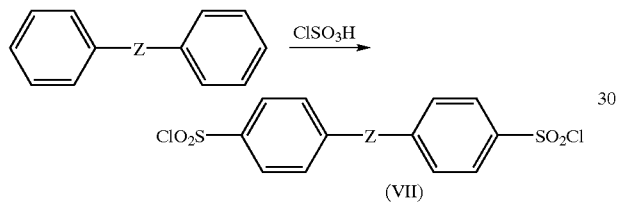

(VII)

Among the compounds represented by formula (I), the compound represented by formula (VII) can be yielded by chlorosulfonating the corresponding phenylalkane or phenylalkene in an organic solvent such as dichloromethane at room temperature. In this case, Z represents the same substituents as those in the aforementioned formulae (II) through (V), but it is unexacting even if there is no substituent S(O)mR on the phenyl group in the formulae (II) through (V).
(Reaction 2)

Among the compounds represented by formula (I), the compound wherein R is represented by a hydrogen atom and m is represented by 0 can be yielded by reducing the compound represented by formula (VII) obtained by Reaction 1 with a reducing agent such as $LiAlH_4$, $NaBH_4$ and the like in the organic solvent such as THF.

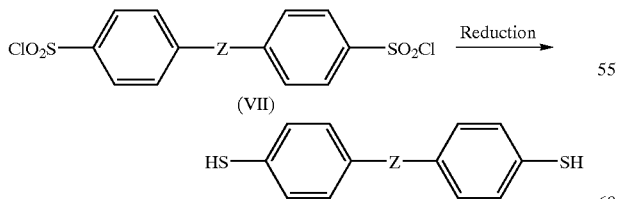

(VII)

(Reaction 3)

Among the compounds represented by formula (I), the compound wherein R is represented by a C1 to C6 alkyl group which may have substituents and m is represented by 0 can be yielded by alkylating the compound given in (Reaction 2) with halogenated alkyl and the like in a solvent such as water, alcohol, ether, THF and the like in the presence of a base such as alcoholate, metallic hydride, organic metal, metalhydroxide and the like. When the mercapto group forms disulfide, alkylation can be carried out after treating with a reducing agent such as $NaBH_4$.

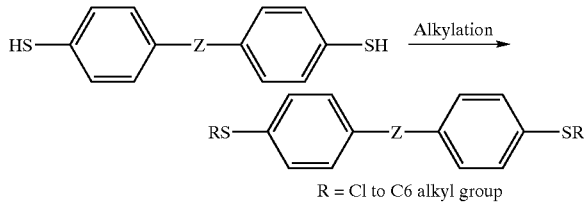

R = Cl to C6 alkyl group (Reaction 4)

Among the compounds represented by formula (I), the compound wherein R is a C1 to C6 alkyl group which may have substituents and m is 1 or 2 can be yielded by oxidizing the compound given in (Reaction 3) with an oxidizing agent such as hydrogen peroxide solution or m-chloroperbenzoic acid in the suitable solvent.

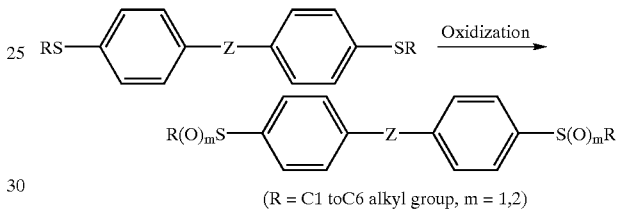

(R = C1 toC6 alkyl group, m = 1,2)

(Reaction 5)

Among the compounds wherein Z is represented by formula (V), for the compound wherein Y is a direct bond, the compound wherein Z is represented by formula (IV) may be first synthesized by (Reaction 2) followed by being reduced by a reducing agent such as alkali metals.

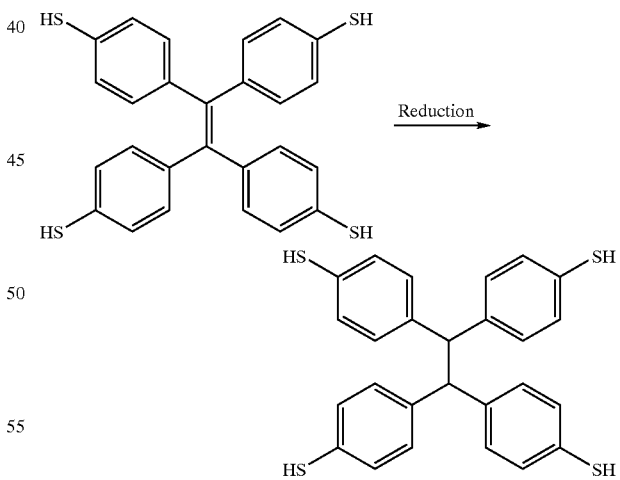

(Reaction 6)

The compounds wherein R are different can be synthesized, for example, as follows.

First, in (Reaction 3), all thiol groups are rendered to cyanoethylthio groups using cyanoethylbromide and the like as halogenated alkyl, and subsequently an equivalent amount of CsOH corresponding to the number of substituents to be substituted and an excess amount of alkyl iodine are added resulting in being capable of substituting parts of cyanoethyl groups with alkyl groups and the like. When an excess amount of CsOH is added thereto to hydrolyze and acid is added, the cyanoethylthio group can be converted to the thiol group.

By the above manipulations, it is possible to partially introduce the target substituent into the thiol group. For example, a case where the methyl group is desired to be introduced into one position is as follows.

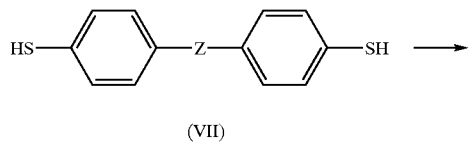

(VII)

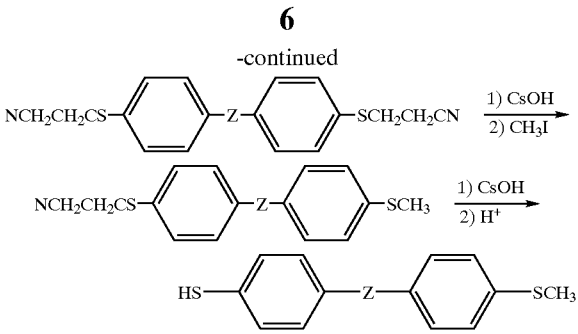

Compounds capable of being synthesized in these ways are shown in Tables 1 through 4.

TABLE 1

| Compound No. | $R^1$ | $R^2$ | $R^3$ | $R^4$ |
|---|---|---|---|---|
| 1-1 | SH | SH | SH | SH |
| 1-2 | SOH | SOH | SOH | SOH |
| 1-3 | $SO_2H$ | $SO_2H$ | $SO_2H$ | $SO_2H$ |
| 1-4 | SMe | SMe | Sme | Sme |
| 1-5 | SOMe | SOMe | SOMe | SOMe |
| 1-6 | $SO_2Me$ | $SO_2Me$ | $SO_2Me$ | $SO_2Me$ |
| 1-7 | $SCF_3$ | $SCF_3$ | $SCF_3$ | $SCF_3$ |
| 1-8 | $SC_2F_5$ | $SC_2F_5$ | $SC_2F_5$ | $SC_2F_5$ |
| 1-9 | $SCF=CF_2$ | $SCF=CF_2$ | $SCF=CF_2$ | $SCF=CF_2$ |
| 1-10 | $SCF_2CF=CF_2$ | $SCF_2CF=CF_2$ | $SCF_2CF=CF_2$ | $SCF_2CF=CF_2$ |
| 1-11 | SPh-4-F | SPh-4-F | SPh-4-F | SPh-4-F |
| 1-12 | SPh-3, 5-$F_2$ | SPh-3, 5-$F_2$ | SPh-3, 5-$F_2$ | SPh-3, 5-$F_2$ |
| 1-13 | SMe | SMe | Sme | SH |
| 1-14 | $SCF_3$ | $SCF_3$ | $SCF_3$ | SH |
| 1-15 | $SC_2F_5$ | $SC_2F_5$ | $SC_2F_5$ | SH |
| 1-16 | $SCF=CF_2$ | $SCF=CF_2$ | $SCF=CF_2$ | SH |
| 1-17 | $SCF_2CF=CF_2$ | $SCF_2CF=CF_2$ | $SCF_2CF=CF_2$ | SH |
| 1-18 | SPh-4-F | SPh-4-F | SPh-4-F | SH |
| 1-19 | SPh-3, 5-$F_2$ | SPh-3, 5-$F_2$ | SPh-3, 5-$F_2$ | SH |
| 1-20 | SMe | SMe | SH | SH |
| 1-21 | $SCF_3$ | $SCF_3$ | SH | SH |
| 1-22 | $SC_2F_5$ | $SC_2F_5$ | SH | SH |
| 1-23 | $SCF=CF_2$ | $SCF=CF_2$ | SH | SH |
| 1-24 | $SCF_2CF=CF_2$ | $SCF_2CF=CF_2$ | SH | SH |
| 1-25 | SPh-4-F | SPh-4-F | SH | SH |
| 1-26 | SPh-3, 5-$F_2$ | SPh-3, 5-$F_2$ | SH | SH |
| 1-27 | SMe | SH | SH | SH |
| 1-28 | $SCF_3$ | SH | SH | SH |
| 1-29 | $SC_2F_5$ | SH | SH | SH |
| 1-30 | SCF=CF2 | SH | SH | SH |
| 1-31 | SCF2CF=CF2 | SH | SH | SH |
| 1-32 | SPh-4-F | SH | SH | SH |
| 1-33 | SPh-3, 5-$F_2$ | SH | SH | SH |

TABLE 2

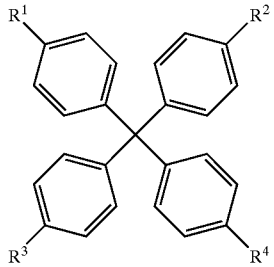

| Compound No. | R¹ | R² | R³ | R⁴ |
|---|---|---|---|---|
| 2-1 | SH | SH | SH | SH |
| 2-2 | SOH | SOH | SOH | SOH |
| 2-3 | $SO_2H$ | $SO_2H$ | $SO_2H$ | $SO_2H$ |
| 2-4 | SMe | SMe | Sme | Sme |
| 2-5 | SOMe | SOMe | SOMe | SOMe |
| 2-6 | $SO_2Me$ | $SO_2Me$ | $SO_2Me$ | $SO_2Me$ |
| 2-7 | $SCF_3$ | $SCF_3$ | $SCF_3$ | $SCF_3$ |
| 2-8 | $SC_2F_5$ | $SC_2F_5$ | $SC_2F_5$ | $SC_2F_5$ |
| 2-9 | $SCF=CF_2$ | $SCF=CF_2$ | $SCF=CF_2$ | $SCF=CF_2$ |
| 2-10 | $SCF_2CF=CF_2$ | $SCF_2CF=CF_2$ | $SCF_2CF=CF_2$ | $SCF_2CF=CF_2$ |
| 2-11 | SPh-4-F | SPh-4-F | SPh-4-F | SPh-4-F |
| 2-12 | SPh-3, 5-$F_2$ | SPh-3, 5-$F_2$ | SPh-3, 5-$F_2$ | SPh-3, 5-$F_2$ |
| 2-13 | SMe | SMe | Sme | SH |
| 2-14 | $SCF_3$ | $SCF_3$ | $SCF_3$ | SH |
| 2-15 | $SC_2F_5$ | $SC_2F_5$ | $SC_2F_5$ | SH |
| 2-16 | $SCF=CF_2$ | $SCF=CF_2$ | $SCF=CF_2$ | SH |
| 2-17 | $SCF_2CF=CF_2$ | $SCF_2CF=CF_2$ | $SCF_2CF=CF_2$ | SH |
| 2-18 | SPh-4-F | SPh-4-F | SPh-4-F | SH |
| 2-19 | SPh-3, 5-$F_2$ | SPh-3, 5-$F_2$ | SPh-3, 5-$F_2$ | SH |
| 2-20 | SMe | SMe | SH | SH |
| 2-21 | $SCF_3$ | $SCF_3$ | SH | SH |
| 2-22 | $SC_2F_5$ | $SC_2F_5$ | SH | SH |
| 2-23 | $SCF=CF_2$ | $SCF=CF_2$ | SH | SH |
| 2-24 | $SCF_2CF=CF_2$ | $SCF_2CF=CF_2$ | SH | SH |
| 2-25 | SPh-4-F | SPh-4-F | SH | SH |
| 2-26 | SPh-3, 5-$F_2$ | SPh-3, 5-$F_2$ | SH | SH |
| 2-27 | SMe | SH | SH | SH |
| 2-28 | $SCF_3$ | SH | SH | SH |
| 2-29 | $SC_2F_5$ | SH | SH | SH |
| 2-30 | $SCF=CF2$ | SH | SH | SH |
| 2-31 | $SCF2CF=CF2$ | SH | SH | SH |
| 2-32 | SPh-4-F | SH | SH | SH |
| 2-33 | SPh-3, 5-$F_2$ | SH | SH | SH |

TABLE 3

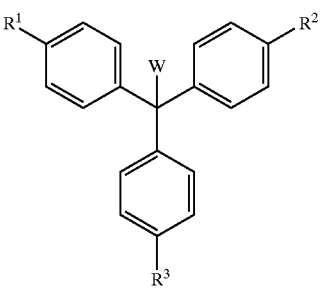

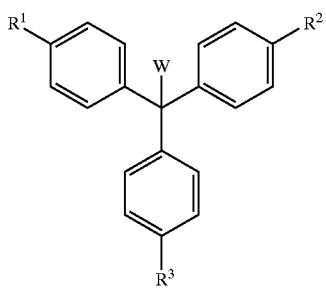
TABLE 3-continued

| Compound No. | R¹ | R² | R³ | W |
|---|---|---|---|---|
| 3-1 | SH | SH | SH | H |
| 3-2 | SOH | SOH | SOH | H |
| 3-3 | $SO_2H$ | $SO_2H$ | $SO_2H$ | H |
| 3-4 | SMe | SMe | Sme | H |
| 3-5 | SOMe | SOMe | SOMe | H |
| 3-6 | $SO_2Me$ | $SO_2Me$ | $SO_2Me$ | H |
| 3-7 | $SCF_3$ | $SCF_3$ | $SCF_3$ | H |
| 3-8 | $SC_2F_5$ | $SC_2F_5$ | $SC_2F_5$ | H |
| 3-9 | $SCF=CF_2$ | $SCF=CF_2$ | $SCF=CF_2$ | H |
| 3-10 | $SCF_2CF=CF_2$ | $SCF_2CF=CF_2$ | $SCF_2CF=CF_2$ | H |

TABLE 3-continued

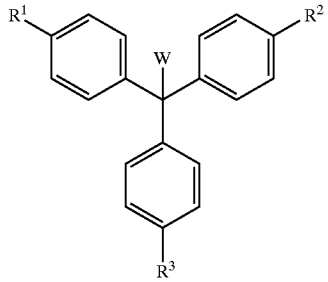

| Compound No. | R¹ | R² | R³ | W |
|---|---|---|---|---|
| 3-11 | SPh-4-F | SPh-4-F | SPh-4-F | H |
| 3-12 | SPh-3, 5-$F_2$ | SPh-3, 5-$F_2$ | SPh-3, 5-$F_2$ | H |
| 3-13 | SMe | SMe | SH | H |
| 3-14 | $SCF_3$ | $SCF_3$ | SH | H |
| 3-15 | $SC_2F_5$ | $SC_2F_5$ | SH | H |
| 3-16 | $SCF=CF_2$ | $SCF=CF_2$ | SH | H |
| 3-17 | $SCF_2CF=CF_2$ | $SCF_2CFCF_2$ | SH | H |
| 3-18 | SPh-4-F | SPh-4-F | SH | H |
| 3-19 | SPh-3, 5-$F_2$ | SPh-3, 5-$F_2$ | SH | H |
| 3-20 | SMe | SH | SH | H |
| 3-21 | $SCF_3$ | SH | SH | H |
| 3-22 | $SC_2F_5$ | SH | SH | H |
| 3-23 | $SCF=CF_2$ | SH | SH | H |
| 3-24 | $SCF_2CF=CF_2$ | SH | SH | H |
| 3-25 | SPh-4-F | SH | SH | H |
| 3-26 | SPh-3, 5-$F_2$ | SH | SH | H |
| 3-27 | SH | SH | SH | Me |
| 3-28 | SH | SH | SH | $CF_3$ |

TABLE 3-continued

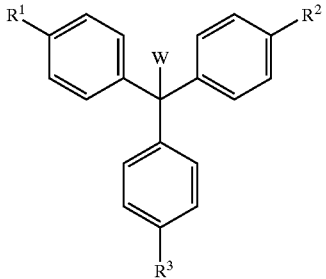

| Compound No. | R¹ | R² | R³ | W |
|---|---|---|---|---|
| 3-29 | $SCF=CF_2$ | $SCF=CF_2$ | $SCF=CF_2$ | Me |
| 3-30 | $SCF_2CF=CF_2$ | $SCF_2CF=CF_2$ | $SCF_2CF=CF_2$ | Me |
| 3-31 | SPh-4-F | SPh-4-F | SPh-4-F | Me |
| 3-32 | SPh-3, 5-$F_2$ | SPh-3, 5-$F_2$ | SPh-3, 5-$F_2$ | Me |
| 3-33 | SMe | SMe | SH | Me |
| 3-34 | $SCF_3$ | $SCF_3$ | SH | Me |
| 3-35 | $SC_2F_5$ | $SC_2F_5$ | SH | Me |
| 3-36 | $SCF=CF_2$ | $SCF=CF_2$ | SH | Me |
| 3-37 | $SCF_2CF=CF_2$ | $SCF_2CFCF_2$ | SH | Me |
| 3-38 | SPh-4-F | SPh-4-F | SH | Me |
| 3-39 | SPh-3, 5-$F_2$ | SPh-3, 5-$F_2$ | SH | Me |
| 3-40 | SMe | SH | SH | Me |
| 3-41 | $SCF_3$ | SH | SH | Me |
| 3-42 | $SC_2F_5$ | SH | SH | Me |
| 3-43 | $SCF=CF_2$ | SH | SH | Me |
| 3-44 | $SCF_2CF=CF_2$ | SH | SH | Me |
| 3-45 | SPh-4-F | SH | SH | Me |
| 3-46 | SPh-3, 5-$F_2$ | SH | SH | Me |

TABLE 4

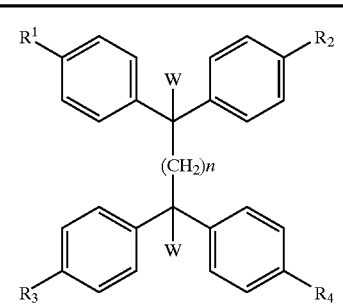

| Compound No. | R¹ | R² | R³ | R⁴ | W | n |
|---|---|---|---|---|---|---|
| 4-1 | SH | SH | SH | SH | H | 0 |
| 4-2 | SOH | SOH | SOH | SOH | H | 0 |
| 4-3 | $SO_2H$ | $SO_2H$ | $SO_2H$ | $SO_2H$ | H | 0 |
| 4-4 | $SCH_3$ | $SCH_3$ | $SCH_3$ | $SCH_3$ | H | 0 |
| 4-5 | $SOCH_3$ | $SOCH_3$ | $SOCH_3$ | $SOCH_3$ | H | 0 |
| 4-6 | $SO_2CH_3$ | $SO_2CH_3$ | $SO_2CH_3$ | $SO_2CH_3$ | H | 0 |

TABLE 4-continued

| Compound No. | R¹ | R² | R³ | R⁴ | W | n |
|---|---|---|---|---|---|---|
| 4-7 | $SCF_3$ | $SCF_3$ | $SCF_3$ | $SCF_3$ | H | 0 |
| 4-8 | $SC_2F_5$ | $SC_2F_5$ | $SC_2F_5$ | $SC_2F_5$ | H | 0 |
| 4-9 | $SCF=CF_2$ | $SCF=CF_2$ | $SCF=CF_2$ | $SCF=CF_2$ | H | 0 |
| 4-10 | $SCF_2CF=CF_2$ | $SCF_2CF=CF_2$ | $SCF_2CF=CF_2$ | $SCF_2CF=CF_2$ | H | 0 |
| 4-11 | SPh-4-F | SPh-4-F | SPh-4-F | SPh-4-F | H | 0 |
| 4-12 | SPh-3, 5-$F_2$ | SPh-3, 5-$F_2$ | SPh-3, 5-$F_2$ | SPh-3, 5-$F_2$ | H | 0 |
| 4-13 | $SCH_3$ | $SCH_3$ | $SCH_3$ | SH | H | 0 |
| 4-14 | $SCF_3$ | $SCF_3$ | $SCF_3$ | SH | H | 0 |
| 4-15 | $SC_2F_5$ | $SC_2F_5$ | $SC_2F_5$ | SH | H | 0 |
| 4-16 | $SCF=CF_2$ | $SCF=CF_2$ | $SCF=CF_2$ | SH | H | 0 |
| 4-17 | $SCF_2CF=CF_2$ | $SCF_2CF=CF_2$ | $SCF_2CF=CF_2$ | SH | H | 0 |
| 4-18 | SPh-4-F | SPh-4-F | SPh-4-F | SH | H | 0 |
| 4-19 | SPh-3, 5-$F_2$ | SPh-3, 5-$F_2$ | SPh-3, 5-$F_2$ | SH | H | 0 |
| 4-20 | $SCH_3$ | $SCH_3$ | SH | SH | H | 0 |
| 4-21 | $SCF_3$ | $SCF_3$ | SH | SH | H | 0 |
| 4-22 | $SC_2F_5$ | $SC_2F_5$ | SH | SH | H | 0 |
| 4-23 | $SCF=CF_2$ | $SCF=CF_2$ | SH | SH | H | 0 |
| 4-24 | $SCF_2CF=CF_2$ | $SCF_2CF=CF_2$ | SH | SH | H | 0 |
| 4-25 | SPh-4-F | SPh-4-F | SH | SH | H | 0 |
| 4-26 | SPh-3, 5-$F_2$ | SPh-3, 5-$F_2$ | SH | SH | H | 0 |
| 4-27 | $SCH_3$ | SH | SH | SH | H | 0 |
| 4-28 | $SCF_3$ | SH | SH | SH | H | 0 |
| 4-29 | $SC_2F_5$ | SH | SH | SH | H | 0 |
| 4-30 | $SCF=CF_2$ | SH | SH | SH | H | 0 |
| 4-31 | $SCF_2CF=CF_2$ | SH | SH | SH | H | 0 |
| 4-32 | SPh-4-F | SH | SH | SH | H | 0 |
| 4-33 | SPh-3, 5-$F_2$ | SH | SH | SH | H | 0 |
| 4-34 | SH | SH | SH | SH | $CH_3$ | 0 |
| 4-35 | $SCF_3$ | $SCF_3$ | $SCF_3$ | $SCF_3$ | $CH_3$ | 0 |
| 4-36 | $SC_2F_5$ | $SC_2F_5$ | $SC_2F_5$ | $SC_2F_5$ | $CH_3$ | 0 |
| 4-37 | $SCF=CF_2$ | $SCF=CF_2$ | $SCF=CF_2$ | $SCF=CF_2$ | $CH_3$ | 0 |
| 4-38 | $SCF_2CF=CF_2$ | $SCF_2CF=CF_2$ | $SCF_2CF=CF_2$ | $SCF_2CF=CF_2$ | $CH_3$ | 0 |
| 4-39 | SPh-4-F | SPh-4-F | SPh-4-F | SPh-4-F | $CH_3$ | 0 |
| 4-40 | SPh-3, 5-$F_2$ | SPh-3, 5-$F_2$ | SPh-3, 5-$F_2$ | SPh-3, 5-$F_2$ | $CH_3$ | 0 |
| 4-41 | SH | SH | SH | SH | H | 1 |
| 4-42 | $SCF_3$ | $SCF_3$ | $SCF_3$ | $SCF_3$ | H | 1 |
| 4-43 | $SC_2F_5$ | $SC_2F_5$ | $SC_2F_5$ | $SC_2F_5$ | H | 1 |
| 4-44 | $SCF=CF_2$ | $SCF=CF_2$ | $SCF=CF_2$ | SCF=CF | H | 1 |
| 4-45 | $SCF_2CF=CF_2$ | $SCF_2CF=CF_2$ | $SCF_2CF=CF_2$ | $SCF_2CF=CF_2$ | H | 1 |
| 4-46 | SPh-4-F | SPh-4-F | SPh-4-F | SPh-4-F | H | 1 |
| 4-47 | SPh-3, 5-$F_2$ | SPh-3, 5-$F_2$ | SPh-3, 5-$F_2$ | SPh-3, 5-$F_2$ | H | 1 |
| 4-48 | SH | SH | SH | SH | $CH_3$ | 1 |
| 4-49 | $SCF_3$ | $SCF_3$ | $SCF_3$ | $SCF_3$ | $CH_3$ | 1 |
| 4-50 | $SC_2F_5$ | $SC_2F_5$ | $SC_2F_5$ | $SC_2F_5$ | $CH_3$ | 1 |
| 4-51 | $SCF=CF_2$ | $SCF=CF_2$ | $SCF=CF_2$ | $SCF=CF_2$ | $CH_3$ | 1 |
| 4-52 | $SCF_2CF=CF_2$ | $SCF_2CF=CF_2$ | $SCF_2CF=CF_2$ | $SCF_2CF=CF_2$ | $CH_3$ | 1 |
| 4-53 | SPh-4-F | SPh-4-F | SPh-4-F | SPh-4-F | $CH_3$ | 1 |
| 4-54 | SPh-3, 5-$F_2$ | SPh-3, 5-$F_2$ | SPh-3, 5-$F_2$ | SPh-3, 5-$F_2$ | $CH_3$ | 1 |

Substances which form molecular compounds together with the sulfur-containing compounds represented by formula (I) in the present invention may be any of those capable of forming the molecular compounds together with such sulfur-containing compounds, and specifically exemplify water, alcohols such as methanol, ethanol, isopropanol, n-butanol, n-octanol, 2-ethylhexanol, allyl alcohol, propargyl alcohol, 1,2-butanediol, 1,3-butanediol, 1,4-butanediol, cyclohexanediol, 2-bromo-2-nitropropane-1,3-diol, 2,2-dibromo-2-nitroethanol, 4-chlorophenyl-3-iodepropargylformal and the like, aldehydes such as formaldehyde, acetaldehyde, n-butylaldehyde, propionaldehyde, benzaldehyde, phthalaldehyde, α-bromcinnamaldehyde, phenylacetaldehyde and the like, ketones such as acetone, methylethyl ketone, diethyl ketone, dibutyl ketone, methylisobutyl ketone, cyclohexanone, acetylacetone, 2-bromo-4'-hydroxyacetophenone and the like, nitriles such as acetonitrile, acrylonitrile, n-butylonitrile, malononitrile, phenylacetonitrile, benzonitrile, cyanopyridine, 2,2- dibromomethylglutarnitrile, 2,3,5,6-tetrachloroisophthalonitrile, 5-chloro-2,4,6-trifluoroisophthalonitrile, 1,2-dibromo-2,4-sicyanobutane and the like, ethers such as diethyl ether, dibutyl ether, tetrahydrofuran, dioxane, tetrahydropyran, dioxirane, trioxane and the like, esters such as methyl acetate, ethyl acetate, butyl acetate, n-heptyl acetate, bis-1,4-bromoacetoxy-2-butene and the like, sulfonamides such as benzene sulfonamide and the like, amides such as N-methylformamide, N,N-dimethylformamide, dicyandiamide, dibromnitrilepropionamide, 2,2-dibromo-3-nitrilepropionamide, N,N-diethyl-m-toluamide and the like, halogenated hydrocarbons such as dichloromethane, chloroform, dichloroethylene, tetrachloroethylene and the like, lactams such as ε-caprolactam and the like, lactones such as 68-caprolactone, oxiranes such as arylglycidyl ether and the like, morpholines, phenols such as phenol, cresol, resorcinol, p-chloro-m-cresol and the like, carboxylic acids and thiocarboxylic acids such as formic acid, acetic acid, propionic acid, oxalic acid, citric acid, adipic acid, tartaric acid, benzoic acid, phthalic acid, salicylic acid and the like, sulfamic acids, thiocarbamic acids, thiosemicarbazides, ureas and thioureas such as urea, phenyl urea, diphenyl urea, thiourea, phenyl thiourea, diphenyl thiourea, N,N-dimethyldichlorophenyl urea and the like, isothioureas, sulfonyl ureas, thiols such as thiophenol, allyl mercaptan, n-butyl mercaptan, benzyl mercaptan and the like, sulfides such as benzylsulfide, butylmethylsulfide and the like, disulfides such as dibutyldisulfide, dibenzyldisulfide, tetramethyltiuramdisulfide and the like, sulfoxides such as dimethylsulfoxide, dibutylsulfoxide, dibenzylsulfoxide and the like, sulfones such as dimethylsulfone, phenylsulfone, phenyl-(2-cyano-2-chlorovinyl)sulfone, hexabromodimethylsulfone, diiodemethylparatorylsulfone and the like, thiocyanates and isothiocyanates such as methyl ester thiocyanate, methyl ester isothiocyanate and the like, amino acids such as glycine, alanine, leucine, lysine, methionine, glutamine and the like, amide and urethane compounds, acid anhydrides, aromatic hydrocarbons such as benzene, toluene, xylene and the like, alkanes, alkenes, alkines, isocyanates such as butyl isocyanate, cyclohexyl isocyanate, phenyl isocyanate and the like, thiocyanates and isothiocyanates such as methylene bisthiocyanate, methylene bisisothiocyanate and the like, nitro compounds such as tris(hydroxymethyl)nitromethane and the like, acyclic aliphatic amines such as ammonia, methylamine, ethylamine, propylamine, butylamine, pentylamine, hexylamine, allylamine, hydroxylamine, ethanol amine, benzylamine, ethylenediamine, 1,2-propanediamine, 1,3-propanediamine, 1,4-butanediamine, 1,5-pentanediamine, 1,6-hexanediamine, diethylenetriamine, triethylenetetramine, tetraethylenepentamine, dipropylenediamine, N,N-dimethylethylenediamine, N,N'-dimethylethylenediamine, N,N-dimethyl-1,3-propanediamine, N-ethyl-1,3-propanediamine, triethylhexamethylenediamine, alkyl-t-monoamine, methanediamine, isophoronediamine, guanidine, N-(2-hydroxypropyl)aminomethanol, cyclic aliphatic amines such as cyclohexylamine, cyclohexanediamine, bis(4-aminocyclohexyl)methane, pyrrolidines, azetidines, piperidines, piperazines such as piperazine, N-aminoethylpiperazine, N,N'-dimethylpiperazine and the like, pyrrolines and the like, aromatic amines such as aniline, N-methylaniline, N,N-dimethylaniline, o-phenylenediamine, m-phenylenediamine, p-phenylenediamine, diaminodiphenylmethane, diaminodiphenylsulfone, m-kylenediamine and the like, modified polyamines such as epoxy compound addition polyamine, Michael addition polyamine, Mannich addition polyamine, thiourea addition polyamine, ketone blockade polyamine and the like, imidazoles such as imidazole, 2-methylimidazole, 2-ethylimidazole, 2-isopropylimidazole, 2-n-propylimidazole, 2-ethyl-4-methylimidazole, 1-benzyl-2-methylimidazole, 2-undecyl-1H-imidazole, 2-heptadecyl-1H-imidazole, 2-phenyl-1H-imidazole, 4-methyl-2-phenyl-1H-imidazole, 1-benzyl-2-methylimidazole and the like, heterocyclic compounds containing nitrogen such as pyrrole, pyridine, picoline, pyrazine, pyridazine, pyrimidine, pyrazole, triazole, benzotriazole, triazine, tetrazole, purine, indole, quinoline, isoquinoline, carbazole, imidazoline, pyrroline, oxazole, piperine, pyrimidine, pyridazine, benzimidazole, indazole, quinazoline, quinoxaline, phthalimide, adenine, cytosine, guanine, uracil, 2-methoxycarbonylbenzimidazole, 2,3,5,6-tetrachloro-4-methanesulfonyl pyridine, 2,2-dithio-bis-(pyridine-1-oxide), N-methyl pyrrolidone, 2-benzimidazole methyl carbamate, 2-pyridinethiol-1-oxide sodium, hexahydro-1,3,5-tris(2-hydroxyethyl)-s-triazine, hexahydro-1,3,5-triethyl-s-triazine, 2-methylthio-4-t-butylaminio-6-cyclopropylamino-s-triazine, N-(fluorodichloromethylthio) phthalimide, 1-bromo-3-chloro-5,5-dimethyl hydantoin, 2-methoxycarbonylbenzimidazole, 2,4,6-trichlorophenylmaleimide and the like, heterocyclic compounds containing oxygen such as furan, furfuryl alcohol, tetrahydro furfuryl alcohol, furfuryl amine, pyran, coumarin, benzofuran, xanthane, benzodioxane and the like, heterocyclic compounds containing both nitrogen and oxygen such as oxazole, isoxazole, benzoxazole, benzoisoxazole, 5-methyl oxazolidine, 4-(2-nitrobutyl)morpholine, 4,4'-(2-ethyl-2-nitrotrimethylene)dimorpholine and the like, heterocyclic compounds containing sulfur such as thiophene, 3,3,4,4-tetrahydrothiophene-1,1-dioxide, 4,5-dichloro-1,2-dithioran-3-one, 5-chloro-4-phenyl-1,2-dithioran-3-one, 3,3,4,4-tetrachlorotetrahydrothiophene-1,1-dioxide and the like, thiazole, benzothiazole, 5-chloro-2-methyl-4-isothiazoline-3-one, 2-methyl-4-isothiazolone-3-one, 4,5-dichloro-3-n-octylisothiazoline-3-one, 2-octyl-4-isothiazoline-3-one, 1,2-benzisothiazoline-3-one, 2-thiocyanomethylbenzothiazole, 2-(4-thiazoryl)benzimidazole, heterocyclic compounds containing nitrogen and sulfur such as 2-thiocyanomethylbenzothiazole and the like of which a component compound is a sulfur-containing compound derivative having triphenyl or tetrakis phenyl, steroids such as cholesterol and the like, alkaloids such as brucine, kinin, theophylline and the like, natural essential oils such as cineol, hinokitiol, menthol, terpineol, borneol, nobour, citral, citronellol, geraniol, menthone, eugenol, linalool, dimethyloctanol and the like, synthetic perfumes such as fragrant olive, jasmine, lemon and the like, vitamins and related compounds such as ascorbic acid, nicotinic acid, nicotinic amide and the like.

The molecular compound of the present invention can be provided by mixing the sulfur-containing compound represented by formula (I) with the above-described substance which forms a molecular compound together with a sulfur-containing compound directly or in the solvent. In the case of a substance with low boiling point or with high vapor pressure, the target molecular compound can be provided by reacting the vapor of these substances to the carboxylate derivative of the present invention. And also, the molecular compound composed of multiple components such as three or more components can be provided by reacting two or more of such substances with the carboxylate derivative of the present invention. Furthermore, the target molecular compound can be provided by first generating the molecular compound of the carboxylate derivative of the present invention with a specific substance, to which another substance is subsequently reacted in the above-described method.

In the molecular compound of the present invention, the ratio of component compounds comprising this sometimes varies depending on its generation condition. It can be verified that the substance provided by the above-described method is certainly the molecular compound by thermal analysis (TG and DTA), infrared absorption spectra (IR), X-ray diffraction pattern, solid NoM spectra and the like. Also, the composition of the molecular compound can be verified by thermal analysis, $^1$H-NMR spectra, high performance liquid chromatography (HPLC), elementary analysis and the like.

The molecular compound of the present invention is preferably crystalline, and in particular, more preferably, a crystalline clathrate compound in terms of performance such as selective separation of useful substances, chemical stabilization, non-volatilization, pulverization for the purpose of stably producing a molecular compound with a constant composition. Under such circumstances, even identical molecular compounds sometimes have crystalline polymorphism. Verification of crystallinity can be performed by mainly examining an X-ray diffraction pattern. Also, the presence of crystalline polymorphism can be verified by thermal analysis, X-ray diffraction pattern, solid NMR and the like. Here, the clathrate compound indicates a substance where there are appropriate sized holes inside of a three dimensional structure made from binding atoms or molecules, and other atoms or molecules penetrate therein by an interaction of a non-covalent bond with a constant composition ratio. Here, it is not necessarily required that the holes are formed by one component compound alone which comprises the clathrate compound. They may be formed only when the clathrate compound is made from two component compounds.

The usage mode of the molecular compound of the present invention is not particularly limited and, for example, two or more types of molecular compounds each made of different component compounds may be used by mixing. Also, the molecular compound of the present invention can be used in combination with the other substances unless such a mixture impairs the target functions. The molecular compound of the present invention can be used by adding an excipient and the like to form granules and tablets. Additionally, it can be used by adding into resins, paints, and their materials and material compositions. The molecular compound of the present invention as it is can be used as such as material of organic synthesis or as a specific reaction field of the molecular compound.

For example, the clathrate compound where the sulfur-containing compound represented by the general formula (I) is a host compound and isothiazolone based insecticide such as 5-chloro-2-methyl-4-isothiazoline-3-one, 2-methyl-4-isothiazoline-3-one and the like, anti-microbial/insecticide/insect repellent agent such as hinokitiol, 1,8-cineole and the like, perfume such as rosemary and the like, anti-foulant such as isothiazolone based compounds and the like, catalysts such as a curing agent for epoxy resins such as phthalic acid anhydride, tetrahydrophthalic acid anhydride, 2-ethyl-4-methylimidazile and the like and curing accelerator for epoxy resins such as 1,8-diazabicyclo(4,5,0)undecene-7 and the like, or organic solvent such as toluene, xylene, pyridine and the like is a guest compound, is newly imparted with functions such as a sustained release, reductions in skin irritations, chemical stabilization, non-volatilization, pulverization, selective separation of useful substances, in addition to actions which the guest compound originally has, and is highly useful as a germicidal agent, anti-microbial agent, insecticidal/insect repellent agent, perfume, anti-foulant, catalyst of curing agent for epoxy resins, or organic solvents.

Since the sulfur-containing compound represented by formula (I) of the present invention also functions as a bidentate ligand, it can form a coordination compound together with metallic ions. The metallic ions which form the coordination compound together with such sulfur-containing compounds can exemplify, for example, gold, platinum, copper, zinc, nickel, iron and the like.

The sulfur-containing compounds of the present invention can be utilized for making ultrafine particle immobilized films of metal, since it is capable of forming self-assembled monolayers and of binding to metal. The ultrafine metallic layer films can be utilized for electronic device production technology, particularly adhesive materials of electronic devices.

Also, the self-assembled monolayers in which water-repellent substituents are introduced can be utilized for water-repellent treatment of devices having ultrafine structures.

In addition to these, utilization for lithography and for oriented films as polyimide alternatives are possible.

BEST MODE FOR CARRYING OUT THE INVENTION

The present invention is described in detail according to examples, but the invention is not limited to these examples.

It can be verified that the resultant substance is a coordination compound by thermal analysis (TG and DTA), infrared absorption spectra (IR), X-ray diffraction pattern and the like. Also, the composition of the coordination compound can be verified by thermal analysis, atomic absorption analysis, elementary analysis and the like.

EXAMPLE 1

Synthesis of 1,1,2,2-tetrakis (4-chlorosulfonylphenyl) ethylene (Compound No. 5)

Under a nitrogen atmosphere, in a 100 mL three-neck round bottomed flask with a stirring bar, 30 mL of anhydrous dichloromethane anhydride and 6 mL of chlorosulfate (90.6 mmol) were placed, and subsequently 3324 mg of tetraphenylethylene (10 mmol) was added in three portions every 10 min in an ice-cooled bath with stirring. At that time, generation of hydrogen chloride was verified. After completing the addition and stirring for 10 min in the ice-cold bath, subsequently the mixture was stirred at room temperature for 24 hours. The reaction mixture was carefully poured into 50 mL of saturated salt solution, and residual solids in the reaction flask were further washed out with the saturated saline solution. This collected solution was extracted with THF (100 mL×5). The extract was thoroughly dehydrated with anhydrous magnesium sulfate, and magnesium sulfate was filtrated out. Then the product was verified by a silica gel thin layer chromatography (developing solvent: chloroform). To this solution, 10 g of silica gel was added and the solvent was distilled followed by drying with vacuum for 1 hour (0.2 Torr) to adsorb the product onto the silica gel. This was subjected to a silica gel column chromatography (φ=40 mm, height=50 mm, eluate:chloroform)

and subsequently recrystallized from THF to afford 2350 mg (2.94 mmol) of colorless crystal as a 1:1 complex of the target compound, 1,1,2,2-tetrakis(4-chlorosulfonylphenyl) ethylene and THF in 29% of yield. When 1,1,2,2-tetrakis (4-chlorosulfonylphenyl)ethylene from which THF was removed was required, this complex was dried with vacuum (0.2 Torr) by heating at 120° C. for 2 hours to yield the target compound.

EXAMPLE 2

Synthesis of 1,1,2,2-tetrakis(4-mercaptophenyl) ethylene (Compound No. 4)

In a 100 mL round-bottomed flask with a stirring bar, 799 mg of the 1:1 complex of 1,1,2,2-tetrakis(4-chlorosulfonylphenyl) ethylene and THF (1 mmol) and 50 mL of THF preliminarily dried with calcium chloride anhydride were placed and stirred to dissolve the substrate. With stirring, 760 mg (20 mmol) of hydrogenated aluminium lithium was slowly added with stirring and cooling in an ice-cold bath. After completing the addition, a reflux condenser was attached followed by warming, and then the mixture was stirred under reflux for 12 hours. The reaction mixture was carefully poured into 50 mL of ice-cooled water, and subsequently acidified with hydrochloric acid (pH<<1). This solution was extracted with dichloromethane (50 mL×3). The resultant dichloromethane solution was extracted with an aqueous solution of 1M sodium hydroxide (50 mL×3). The resultant aqueous solution was acidified with hydrochloric acid (pH<<1), and extracted with dichloromethane (50 ml×3). The extract was thoroughly dehydrated with anhydrous sodium sulfate, which is filtrated out, and then the product was verified by a silica gel thin layer chromatography (eluate: carbon tetrachloride). Subsequently, 2 g of silica gel was added to this solution, and the solvent was distilled to adsorb the product onto the silica gel. This was subjected to a silica gel column chromatography ($\phi$=25 mm, height=50 mm, eluate: carbon tetrachloride), and recrystallized from carbon tetrachloride to afford 399 mg (0.866 mmol) of the target compound, 1,1,2,2-tetrakis(4-mercaptophenyl)ethylene as a pale yellow crystal in 87% of yield.

EXAMPLE 3

Synthesis of 1,1,2,2-tetrakis(4-mercaptophenyl) ethane (Compound No. 8)

Under a nitrogen atmosphere, anhydrous THF was added to a 20 ml round-bottomed flask equipped with gas inlet tube, in which 124 mg (0.269 mmol) of 1,1,2,2-tetrakis(4-mercaptophenyl)ethylene was placed, to dissolve the substrate. This was cooled to –78° C., and ammonia gas was introduced from the tube until 10 mL of liquid was appeared. Subsequently 49 mg (2.15 mmol) of sodium was added with stirring, and it was confirmed that the reaction solution became a deep blue color (a liquid ammonia was further added if the solution was not changed to blue). After stirring at –78° C. for one hour, 115 mg (2.15 mmol) of ammonium chloride was added, and the liquid ammonia was evaporated by slowly warming. After 10 ml of water was added to the reaction mixture, it was acidified with hydrochloric acid (pH<<1). The mixture was extracted with dichloromethane (20 mL×3), subsequently the resultant dichloromethane solution was extracted with an aqueous solution of IN sodium hydroxide (20 mL×3), further the resultant aqueous solution was acidified with hydrochloric acid (pH<<1), and then was extracted with dichloromethane (20 mL×3). The extract was thoroughly dehydrated with anhydrous sodium sulfate, from which sodium sulfate is separated by filtration, and then the product was verified by a silica gel thin layer chromatography (eluate: chloroform). Subsequently, 1 g of silica gel was added to this solution, and the solvent was distilled to adsorb the product onto the silica gel. This was subjected to a silica gel column chromatography ($\phi$=15 mm, height=50 mm, eluate: chloroform), and recrystallized from chloroform to afford 81 mg (0.175 mmol) of the target compound, 1,1,2,2-tetrakis(4-mercaptophenyl)ethane as a colorless crystal in 65% of yield.

EXAMPLE 4

Synthesis of 1,1,2,2-tetrakis(4-chlorosulfonylphenyl) methane (No. 9)

Under a nitrogen atmosphere, 30 mL of anhydrous dichloromethane and 6 mL (90.6 mmol) of chlorosulfate were added to a 100 mL three-neck round-bottomed flask with a stirring bar, and subsequently 3204 mg (10 mmol)of tetraphenylmethane was added in three portions every 10 min with stirring in an ice-cooled bath. At that time, generation of hydrogen chloride was verified. After completing the addition and stirring for 10 min in the ice-cooled bath, the mixture was stirred at room temperature for 24 hours. The reaction mixture was carefully poured into 50 ml of a saturated salt solution, and residual solids in the reaction flask were washed out with the saturated salt solution. This collected aqueous solution was extracted with THF (100 mL×5). The extract was thoroughly dehydrated with anhydrous magnesium sulfate, from which magnesium sulfate was separated by filtration, and subsequently, the product was verified by a silica gel thin layer chromatography (eluate: chloroform). Then, 10 g of silica gel was added to this solution and the solvent was distilled followed by drying with vacuum for 1 hour (0.2 Torr) to adsorb the product onto the silica gel. This was purified by a silica gel column chromatography ($\phi$=40 mm, height=50 mm, eluate: chloroform) and subsequently recrystallized from THF to afford 974 mg (1.36 mmol) of colorless crystal as a 1:0.75 complex of the target compound, 1,1,2,2-tetrakis(4-chlorosulfonylphenyl)methane and THF in 14% of yield.

EXAMPLE 5

Synthesis of 1,1,2,2-tetrakis(4-mercaptophenyl) methane (Compound No. 10)

To a 100 mL round-bottomed flask with a stirring bar, 315 mg (0.410 mmol) of the 1:0.75 complex of 1,1,2,2-tetrakis (4-chlorosulfonylphenyl)methane and THF, and 20 mL of THF preliminarily dried with anhydrous calcium chloride were added and stirred to dissolve the substrate. With stirring, 304 mg (8 mmol) of lithium aluminium hydride was slowly added with cooling in an ice-cold bath. After completing the addition, a reflux condenser was attached followed by warming, and then the mixture was stirred under reflux for 14.5 hours. The reaction solution was carefully poured into 50 mL of ice-cooled water, and subsequently acidified with hydrochloric acid (pH<<1). This solution was extracted with dichloromethane (50 mL×3). The resultant dichloromethane solution was extracted with an aqueous solution of 1M sodium hydroxide (50 mL×3). The resultant aqueous solution was acidified with hydrochloric acid (pH<<1), and extracted with dichloromethane (50 ml×3). The extract was thoroughly dried over anhydrous sodium sulfate, from which sodium sulfate is separated by filtration, and then the product was verified by a silica gel thin layer chromatography (eluate: carbon tetrachloride). Subsequently, 1 g of silica gel was added to this solution, and the solvent was distilled to adsorb the product onto the silica gel. This was purified by a silica gel column chromatography (φ=20 mm, height=50 mm, eluate: carbon tetrachloride), and recrystallized from carbon tetrachloride to afford 133 mg (0.296 mmol) of the target compound, 1,1,2,2-tetrakis(4-mercaptophenyl)methane as a colorless crystal in 72% of yield.

EXAMPLE 6

Synthesis of 1,1,2,2-tetrakis(4-cyanoethylthiophenyl) ethylene (Compound No. 11)

1,1,2,2-tetrakis(4-mercaptophenyl) ethylene (0.5 mmol) made in Example 2 was added to 30 ml of THF, and 160 mg (4.0 mmol) of sodium hydride and 0.35 mL (4.0 mmol) of 3-bromopropionitrile were added with stirring in an ice-cooled bath followed by being refluxed at 85° C. for 24 hours. After solvent was evaporated, ice-cooled water was added to the residue, the mixture was acidified with hydrochloric acid, and then was extracted with dichloromethane. The extract was dehydrated with anhydrous magnesium sulfate. Subsequently, it was subjected to a silica gel column chromatography (φ40 mm, height=50 mm, developing solvent: ethyl acetate: chloroform=1:15), and was recrystallized from chloroform and carbon tetrachloride to afford the target compound.

The compounds obtained by the above-described methods and the compounds obtained by the same methods are shown in Table 5.

TABLE 5

| Compound No. | Chemical structure | Values of physical properties |
|---|---|---|
| 1 | (structure: tris(4-mercaptophenyl)methane) | 1H NMR(400 MHZ, CDCl$_8$) δ 7.18(d, J = 8.2 Hz, 6H, ArH)$_1$ 6.93(d, J = 8.2 Hz, 6H, ArH), 5.35(s, 1H, CH), 3.40 (s, 3H, SH); $^{18}$C NMR(101 MHz, CDCl$_8$) δ 141.0, 130.0, 129.5, 126.6, 128.7, 55.1 |
| 2 | (structure: tris(4-chlorosulfonylphenyl)methane) | $^1$H NMR(400 MHz, CDCl$_3$) δ 8.06(d, J = 8.6 HZ, 6H, ArH), 7.37(d, J = 8.6 Hz, 6H, ArH)$_1$ 5.87(s, 1H, CH); $^{13}$C NMR(101 MHz, CDCl$_2$) δ 148.1, 143.7, 130.5, 127.9, 56.3; IR(KBr) 3094, 1589, 1491, 1408, 1373, 1177(SO$_2$), 1083, 1016, 861, 823, 748, 681, 627, 554 cm$^{-1}$ |
| 3 | (structure: tris(4-methylthiophenyl)methane) | $^1$H NMR(400 MHz, CDCl$_3$) δ 7.17(d, J = 8.3 Hz, 6H, ArH), 7.00(d, J → 8.3 Hz, 6H, ArH), 5.40(s, 1H, CH), 2.45(s, 9H, CH$_3$); $^{13}$C NMR(101 MHz, CDCl$_3$) δ 140.6, 136.3, 129.7, 126.6, 55.2, 15.9; IR(KBr) 2918, 1594, 1492, 1433, 1403, 1282, 1192, 1091, 1015, 965, 814, 782, 531 cm$^{-1}$ |
| 4 | (structure: 1,1,2,2-tetrakis(4-mercaptophenyl)ethylene) | M.P. 239.0° C. $^1$H NMR(400 MHZ, CDCl$_3$) δ 7.00 (d, J = 8.1 HZ, 8H, ArH), 6.84(d, J = 8.1 Hz, 8H, ArH), 3.38(s, 4H, SH); $^{13}$C NMR(101 MHz, CDCl$_3$) δ 140.7, 139.4, 131.9, 129.2, 128.8; IR(KBr) 2562(SH), 1591, 1492, 1400, 1099, 1016, 820, 795, 524, 498 cm$^{-1}$ |

TABLE 5-continued

| Compound No. | Chemical structure | Values of physical properties |
|---|---|---|
| 5 | (tetrakis(4-chlorosulfonylphenyl)ethylene) | M.P. 327.0° C. (Decomposition): <br> $^1$H NMR(400 MHz, THF-d$_3$) δ 7.98(d, J = 8.4 Hz, 8H, ArH), 7.46(d, J = 8.4 Hz, 8H, ArH); <br> $^{13}$C NMR(101 MHz, THF-d$_3$) δ 148.9, 144.6, 142.8, 133.3, 128.1; <br> IR(KBr) <br> 3091, 1588, 1490, 1379, 1286, 1175(SO$_2$), 1116, 1081, 1015, 874, 829, 745, 697, 676, 648, 626, 555, 496 cm$^{-1}$; |
| 6 | (tetrakis(4-methylthiophenyl)ethylene) | M.P. 216.4° C; <br> $^1$H NMR(400 MHz, CDCl$_3$) δ 6.97(d, J = 8.4 Hz, 8H, ArH), 6.91(d, J = 8.4 Hz, 8H, ArH), 2.43(s, 12H, CH$_3$); <br> $^{13}$C NMR(101 MHz, CDCl$_3$) δ 140.3, 139.4, 136.6, 131.8, 125.5, 15.4; <br> IR(KBr) <br> 2916, 1592, 1492, 1435, 1397, 1185, 1113, 1092, 1015, 963, 859, 807, 791, 735, 666, 567, 523, 501 cm$^{-1}$; |
| 7 | (tetrakis(4-methylsulfonylphenyl)ethylene) | M.P. 173.0° C; (Decomposition): <br> $^1$H NMR(400 MHz, CDCl$_3$) δ 7.77(d, J = 8.2 Hz, 8H, ArH), 7.20(d, J = 8.2 Hz, 8H, ArH), 3.05 (s, 12H, CH$_3$); <br> $^{13}$C NMR(101 MHz, CDCl$_3$) δ 146.8, 141.4, 140.0, 131.8, 127.6, 44.3; <br> IR(KBr) <br> 2927, 1593, 1399, 1302, 1150, (SO$_2$), 1089, 1015, 961, 834, 771, 734, 662, 526 cm$^{-1}$; |
| 8 | (tetrakis(4-mercaptophenyl)methane analog) | M.P. 293.5° C. (Decomposition): <br> $^1$H NMR(400 MHz, CDCl$_3$) δ 7.18(d, J = 8.2 Hz, 6H, ArH), 6.93(d, J = 8.2 Hz, 6H, ArH), 5.35(s, 1H, CH), 3.40(s, 3H, SH); <br> $^{13}$C NMR(101 MHz, CDCl$_3$) δ 141.0, 130.0, 129.5, 126.6, 128.7, 55.1 <br> IR(KBr) <br> 2549(SH), 1492, 1404, 1103, 1015, 807, 786, 655, 528, 497 cm$^{-1}$ |
| 9 | (tetrakis(4-chlorosulfonylphenyl)methane) | M.P. 285.8° C. (Decomposition); <br> $^1$H NMR(400 MHz, CDCl$_3$) δ δ7.54 (d, J = 8.3 Hz, 8H, ArH), 7.06 (d, J = 8.3 Hz, 8H, ArH); <br> $^{13}$C NMR(101 MHz, CDCl$_3$) δ146.4, 145.6, 130.1, 125.1, 64.0; <br> IR(KBr)3443, 3096, 1588, 1489, 1406, 1387(SO2), 1293, 1180(SO2), 1085, 1014, 824, 747, 734, 701, 630 and 555 cm-1; |
| 10 | (tetrakis(4-mercaptophenyl)methane) | M.P. 198.3° C. (Decomposition): <br> $^1$H NMR(400 MHz, CDCl$_3$) δ7.13 (d, J = 8.5 Hz, 8H, ArH), 7.00 (d, J = 8.5 Hz, 8H, ArH), 3.39 (s, 4H, SH); <br> $^{13}$C NMR(101 MHz, CDCl$_3$) δ143.7, 131.492, 131.457, 128.7, 63.3; <br> IR(KBr) 1589, 1562, 1486, 1402, 1193, 1102, 1016, 810, 544, 525 cm-1; |

TABLE 5-continued

| Compound No. | Chemical structure | Values of physical properties |
|---|---|---|
| 11 | 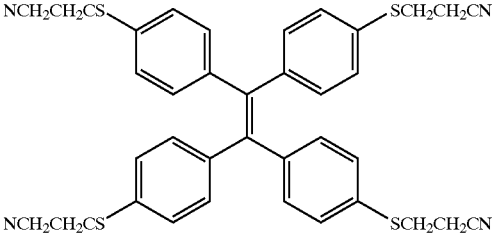 | M.P. 145.0 (Decomposition):<br>$^1$H NMR(400 MHz, CDCl$_3$) δ 7.15(d, J = 8.3Hz, 8H, ArH), 6.96(d, J = 8.3 Hz, 8H, ArH), 3.10(t, J = 7.2 Hz, 8H, CH$_2$), 2.59(t, J = 7.2 Hz, 8H, CH$_2$); $^{13}$C NMR(101 MHz, CDCl$_3$) 67 142.0, 141.0, 182.2, 182.0, 130.1, 117.8, 29.6, 18.2<br>IR(KBr)<br>3449, 2549(CN), 1589, 1492, 1420, 1399, 1285, 1090, 1014, 959, 904, 864, 827, 801, 742, 676, 522 cm$^{-1}$ |

EXAMPLE 7

Synthesis of 1,1,2-tris(4-cyanoethylthiophenyl)-2-(4-methylthiophenyl)ethylene (Compound No. 12)

In a 200 mL round-bottomed flask equipped with a dropping funnel, 336 mg (0.5 mmol) of 1,1,2,2-tetrakis(4-cyanoethylthiophenyl)ethylene was dissolved in 50 mL of acetonitrile. In the dropping funnel, a solution of 75 mg (0.5 mmol) of cesium hydroxide which was predissolved in 10 mL of methanol was diluted with 50 mL of acetonitrile. The resultant solution is slowly added over 1.5 hours from the dripping funnel. After stirring for one hour at room temperature, 0.7 mL (11 mmol) of methyl iodine was added to the mixture followed by stirring for an additional one hour. The reaction mixture was poured into 50 mL of an aqueous solution of saturated sodium hydrogen sulfite, then extracted with dichloromethane (50 mL×3). The extract was thoroughly dried over anhydrous magnesium sulfate, from which magnesium sulfate was separated by filtration. Then, the product was verified by a silica gel thin layer chromatography (mobile phase: ethyl acetate: chloroform=1:15). Subsequently, 2 g of silica gel was added to this solution, and the solvent is eliminated to adsorb the product onto the silica gel. This was purified by a silica gel column chromatography (φ=25 mm, height=80 mm, mobile phase: ethyl acetate: chloroform=1:15) to afford 1,1,2-tris(4-cyanoethylthiophenyl)-2-(4-methylthiophenyl) ethylene as yellow crystal in 56% of yield.

Yellow crystals; mp. 117.5° C.;
1H-NMR(400 MHz, CDCl$_3$) δ2.44(s, 3H, CH3), 2.57(t, J=7.3 Hz, 2H, CH2), 2.580(t, J=7.2 Hz, 2H, CH2), 2.584 (t, J=7.2 Hz, 2H, CH2), 3.10(t, J=7.1 Hz, 6H, CH2), 6.89(d, J=8.5 Hz, 2H, ArH), 6.95(d, J=8.3 Hz, 2H, ArH), 6.96(d, J=8.2 Hz, 2H, ArH), 6.98(d, J=8.2 Hz, 2H, ArH), 6.99(d, J=8.5 Hz, 2H, ArH), 7.138(d, J=8.2 Hz, 2H, ArH), 7.145(d, J=8.3 Hz, 2H, ArH), 7.15(d,J=8.2 Hz, 2H, ArH);
13C-NMR(101 MHz, CDCl$_3$) δ15.2, 18.1, 18.16, 18.19, 29.74, 29.77, 117.85, 117.89, 125.4, 130.15, 130.23, 130.28, 131.6, 131.8, 131.93, 131.96, 132.11, 132.13, 132.2, 137.6, 139.2, 139.3, 140.6, 142.4, 142.5;
IR(KBr) 3446, 2923, 2250(CN), 1590, 1492, 1418, 1398, 1283, 1090, 1013, 957, 826, 799, 739, 572, 403 cm$^{-1}$.

EXAMPLE 8

Synthesis of 1,1,2-tris(4-mercaptophenyl)-2-(4-methylthiophenyl)ethylene (Compound No. 13)

To a 50 mL round-bottomed flask with a stirring bar, 127 mg (0.02 mmol) of the compound No. 12 prepared in Example 7 and 30 mL of acetonitrile were added and stirred to dissolve the substrate. Subsequently, a solution in which 270 mg (1.8 mmol) of cesium hydroxide is dissolved in 5 mL of methanol was added followed by stirring at room temperature for one hour. The reaction solution was poured into water (pH<1) acidified with hydrochloric acid and extracted with dichloromethane (50 mL×3). Then, this dichloromethane solution was extracted with an aqueous solution of 1N sodium hydroxide (50 mL×3). Further, this aqueous solution was acidified (pH<1) with hydrochloric acid and extracted with dichloromethane (50 mL×3). The extract was thoroughly dehydrated with anhydrous magnesium sulfate, from which magnesium sulfate is separated by filtration. Subsequently, the product is verified by a silica gel thin layer chromatography (mobile phase: chloroform). Then, 2 g of silica gel was added to this solution, and the solvent is eliminated to adsorb the product onto the silica gel. This was purified by a silica gel column chromatography (φ25 mm, height=50 mm, mobile phase: chloroform) to afford 1,1,2-tris(4-mercaptophenyl)-2-(4-methylthiophenyl) ethylene as a yellow crystal in 27% of yield.

Yellow crystals; mp. 215.8° C.;
1H-NMR(400 MHz, CDCl$_3$) δ2.42(s, 3H, CH3), 3.37(s, 1H, SH), 3.38(s, 2H, SH), 6.83–6.89(m, 8H, ArH), 6.96–6.7.01(m, 8H, ArH);
13C-NMR(101 MHz, CDCl$_3$) δ15.3, 125.5, 128.8(2C), 129.06, 129.08, 131.7, 132.0(2C), 136.9, 139.2, 139.7, 139.9, 140.86, 140.88;
IR(KBr) 3449, 2920, 2559(SH), 1591, 1492, 1399, 1184, 1096, 1016, 862, 818, 797, 739, 524, 499 cm$^{-1}$.

EXAMPLE 9

Production of a molecular compound comprising 1,1,2,2-tetrakis(4-mercaptophenyl)ethane as a component compound 0.13 g of 1,1,2,2-tetrakis(4-mercaptophenyl)ethane was dissolved in 3 ml of pyridine with heating, and the solution was left to stand at room temperature for one hour. Precipitated crystals were collected by filtration, and dried under reduced pressure at 40° C. for one hour using a rotary vacuum pump to afford the molecular compound composed of 1,1,2,2-tetrakis (4-mercaptophenyl) ethane and pyridine at a composition ratio of 1:3 (molar ratio). Next, using N,N-dimethylformamide instead of pyridine, the same manipulation was carried out, but after leaving it to stand at room temperature for 24 hours, N,N-dimethylformamide was distilled under reduced pressure. And the residue was dried under reduced pressure at 80° C. for one hour using a rotary vacuum pump to afford the molecular compound composed of 1,1,2,2-tetrakis(4-mercaptophenyl)ethane and N,N-dimethylformamide at a composition ratio of 1:1 (molar ratio).

Industrial Applicability

The molecular compound comprising the novel sulfur-containing compound of the present invention as the component compound can be prepared by simple manipulation, and can impart functions such as chemical stabilization, non-volatilization, sustained release formulation, pulverization and the like for various materials as well as performing collection and selective separation of specific materials. The self-assembled monolayers according to the compound of the present invention are capable of being applied for electronic device making technology. Therefore, the present invention is capable of being utilized in extremely broad spheres and its significance is remarkable within the industry.

What is claimed is:

1. A sulfur-containing compound represented by formula (VI):

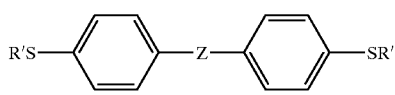

wherein R' each independently represents a hydrogen atom, a C1 to C6 alkyl group which may have substituents, C2 to C6 alkenyl group which may have substituents, or an aryl group which may have substituents;

Z represents the following formulae (IIA) through (V):

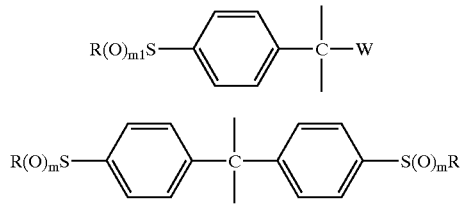

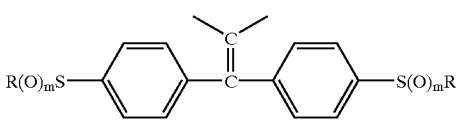

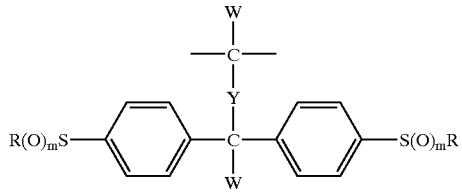

W represents a hydrogen atom or a C1 to C6 alkyl group which may have substituents;

Y represents a direct bond, an alkylene group having 1 to 3 carbons or a phenylene group;

R represents R'; m represents an integer of 0, 1 or 2; and m1 represents an integer of 1 or 2.

2. A sulfur-containing compound represented by formula (VIII):

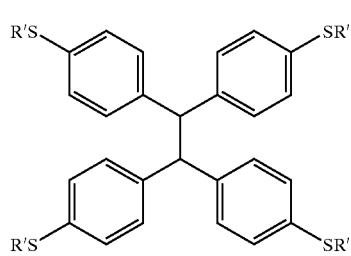

wherein R' each independently represents a hydrogen atom, a C1 to C6 alkyl group which may have substituents, a C2 to C6 alkenyl group which may have substituents, or an aryl group which may have substituents.

* * * * *

UNITED STATES PATENT AND TRADEMARK OFFICE
CERTIFICATE OF CORRECTION

PATENT NO. : 6,740,782 B2
APPLICATION NO. : 10/221757
DATED : May 25, 2004
INVENTOR(S) : Ryu Sato et al.

It is certified that error appears in the above-identified patent and that said Letters Patent is hereby corrected as shown below:

On title page, item 75 Inventors
  replace "City of first named inventor"
  with --Iwate--.

Col. 3, line 50
  replace "NaBH4"
  with --$NaBH_4$--

Col. 7, Table 2, Compound No. 2-30, under heading $R^1$
  replace "SCF=CF2"
  with --$SCF=CF_2$--

Col. 7, Table 2, Compound No. 2-31, under heading $R^1$
  replace "SCF2CF=CF2"
  with --$SCF_2CF=CF_2$--

Col. 9, Table 3, Compound No. 3-17, under heading $R^2$
  replace "$SCF_2CFCF_2$"
  with --$SCF_2CF=CF_2$--

Col. 10, Table 3, Compound No. 3-37, under heading $R^2$
  replace "$SCF_2CFCF_2$"
  with --$SCF_2CF=CF_2$--

Col. 11, Table 4, Compound No. 4-44, under heading $R^4$
  replace "SCF=CF"
  with --$SCF=CF_2$--

Col. 13, line 16
  replace "68-caprolactone"
  with --ε-caprolactone--

Col. 15, line 13
  replace "NoM"
  with --NMR--

UNITED STATES PATENT AND TRADEMARK OFFICE
CERTIFICATE OF CORRECTION

PATENT NO. : 6,740,782 B2
APPLICATION NO. : 10/221757
DATED : May 25, 2004
INVENTOR(S) : Ryu Sato et al.

It is certified that error appears in the above-identified patent and that said Letters Patent is hereby corrected as shown below:

Col. 20, Table 5, Compound No. 1, under heading Values of physical properties replace "entire formula chain"
with --1H NMR(400MH$_Z$, CDCL$_3$) δ 7.18(d,J=8.2H$_z$, 6H, ArH),
6.93(d,J=8.2H$_Z$, 6H, ArH), 5.35(s, 1H, CH), 3.40(s, 3H, SH);
$^{13}$C NMR(101MH$_Z$, CDCL$_3$) δ
141.0, 130.0, 129.5, 126.6, 128.7, 55.1--

Col. 20, Table 5, Compound No. 2, under heading Values of physical properties replace "entire formula chain"
with --1H NMR(400MH$_Z$, CDCL$_3$) δ 8.06(d,J=8.6H$_Z$, 6H, ArH),
7.37(d,J=8.6H$_Z$, 6H, ArH), 5.87(s, 1H, CH);
$^{13}$C NMR(101MH$_Z$, CDCL$_3$) δ 148.1, 143.7, 130.5, 127.9, 56.3;
IR(KBr)
3094, 1589, 1491, 1408, 1373, 1177(SO$_2$), 1083, 1016, 861, 823,
748, 681, 627, 554cm-$^1$--

Col. 20, Table 5, Compound No. 3, under heading Values of physical properties replace "entire formula chain"
with --1H NMR(400MH$_Z$, CDCL$_3$) δ 7.17(d,J=8.3H$_Z$, 6H, ArH),
7.00(d,J=8.3H$_Z$, 6H, ArH), 5.40(s, 1H, CH), 2.45(s, 9H, CH$_3$);
$^{13}$C NMR(101MH$_Z$, CDCL$_3$ δ
140.6, 136.3, 129.7, 126.6, 55.2, 15.9;
IR(KBr)
2918, 1594, 1492, 1433, 1403, 1282, 1192, 1091, 1015, 965,
814, 782, 531cm-$^1$--

Col. 20, Table 5, Compound No. 4, under heading Values of physical properties replace "entire formula chain"
with --M.P. 239.0°C.
1H NMR(400MH$_Z$, CDCL$_3$) δ 7.00(d,J=8.1H$_Z$, 8H, ArH),
6.84(d,J=8.1H$_Z$, 8H, ArH), 3.38(s, 4H, SH);
$^{13}$C NMR(101MH$_Z$, CDCL$_3$) δ 140.7, 139.4, 131.9, 129.2, 128.8;
IR(KBr)
2562(SH), 1591, 1492, 1400, 1099, 1016, 820, 795, 524, 498cm-$^1$--

UNITED STATES PATENT AND TRADEMARK OFFICE
CERTIFICATE OF CORRECTION

PATENT NO. : 6,740,782 B2
APPLICATION NO. : 10/221757
DATED : May 25, 2004
INVENTOR(S) : Ryu Sato et al.

It is certified that error appears in the above-identified patent and that said Letters Patent is hereby corrected as shown below:

Col. 22, Table 5, Compound No. 6, under heading Values of physical properties replace "entire formula chain"
with --M.P. 216.4°C.
1H NMR(400MH$_Z$, CDCL$_3$) δ 6.97(d,J=8.4H$_Z$, 8H, ArH),
6.91(d,J=8.4H$_Z$, 8H, ArH), 2.43(s, 12H, CH$_3$);
$^{13}$C NMR(101MH$_Z$, CDCL$_3$) δ
140.3, 139.4, 136.6, 131.8, 125.5, 15.4;
IR(KBr)
2916, 1592, 1492, 1435, 1397, 1185, 1113, 1092, 1015, 963, 859,
807, 791, 735, 666, 567, 523, 501cm-$^1$;--

Col. 22, Table 5, Compound No. 7, under heading Values of physical properties replace "entire formula chain"
with --M.P. 173.0°C. (Decomposition):
1H NMR(400MH$_Z$, CDCL$_3$) δ 7.77(d,J=8.2H$_Z$, 8H, ArH),
7.20(d,J=8.2H$_Z$, 8H, ArH), 3.05(s, 12H, CH$_3$);
$^{13}$C NMR(101MH$_Z$, CDCL$_3$) δ
146.6, 141.4, 140.0, 131.8, 127.6, 44.3;
IR(KBr)
2927, 1593, 1399, 1302, 1150, (SO$_2$), 1089, 1015, 961, 834, 771,
734, 662, 526cm-$^1$;--

Col. 24, Table 5, Compound No. 11, under heading Values of physical properties replace "entire formula chain"
with --M.P. 145.0 (Decomposition);
1H NMR(400MH$_Z$, CDCL$_3$) δ 7.15(d,J=8.3H$_Z$, 8H, ArH),
6.96(d,J=8.3H$_Z$, 8H, ArH),
3.10(t,J=7.2H$_Z$, 8H, CH$_2$), 2.59(t,J=7.2H$_Z$, 8H, CH$_2$);
$^{13}$C NMR(101MH$_Z$, CDCL$_3$) δ
142.0, 141.0, 132.2, 132.0, 130.1, 117.8, 29.6, 18.2
IR(KBr)
3449, 2549(CN), 1589, 1492, 1420, 1399, 1285, 1090, 1014, 959,
904, 864, 827, 801, 742, 575, 522cm-$^1$--

UNITED STATES PATENT AND TRADEMARK OFFICE
CERTIFICATE OF CORRECTION

PATENT NO. : 6,740,782 B2
APPLICATION NO. : 10/221757
DATED : May 25, 2004
INVENTOR(S) : Ryu Sato et al.

It is certified that error appears in the above-identified patent and that said Letters Patent is hereby corrected as shown below:

Col. 25, line 31
  replace "C2 to C6 alkenyl"
  with --a C2 to C6 alkenyl--

Signed and Sealed this

Nineteenth Day of February, 2008

JON W. DUDAS
*Director of the United States Patent and Trademark Office*